US00PP23349P2

(12) United States Plant Patent
Oliver

(10) Patent No.: US PP23,349 P2
(45) Date of Patent: Jan. 22, 2013

(54) ***HEUCHERA* PLANT NAMED 'STAINLESS STEEL'**

(50) Latin Name: *Heuchera* hybrid
Varietal Denomination: Stainless Steel

(75) Inventor: Charles Oliver, Scottdale, PA (US)

(73) Assignee: Plants Nouveau, LLC, Charleston, SC (US)

( * ) Notice: Subject to any disclaimer, the term of this patent is extended or adjusted under 35 U.S.C. 154(b) by 34 days.

(21) Appl. No.: 13/136,164

(22) Filed: Jul. 25, 2011

(51) Int. Cl.
*A01H 5/00* (2006.01)

(52) U.S. Cl. ..... Plt./440

(58) Field of Classification Search ..... Plt./440
See application file for complete search history.

*Primary Examiner* — Susan McCormick Ewoldt
(74) *Attorney, Agent, or Firm* — Penny J. Aguirre

(57) ABSTRACT

A new cultivar of *Heuchera*, 'Stainless Steel', is characterized by its foliage that emerges silver in color and heavily suffused with red-purple and matures to silver with green veins, lower leaf surface is dark red-purple, its flowers that are comparatively large, well shaped, and white in color, its well-proportioned plant form, its evergreen foliage that is weather resistant with good tolerance to wind and rain, and its good garden performance.

2 Drawing Sheets

Botanical classification: *Heuchera* hybrid.
Cultivar designation: 'Stainless Steel'.

BACKGROUND OF THE INVENTION

The present invention relates to a new and distinct cultivar of hybrid *Heuchera*, botanically known as a *Heuchera* of hybrid origin and is hereinafter referred to by the cultivar name 'Stainless Steel'.

The new cultivar derived from a controlled breeding program conducted by the inventor in Scottsdale, Pa. The goal of the breeding program was to obtain unique cultivars of *Heuchera* that exhibit showy flowers, colorful foliage, and good vigor. The inventor made a cross in May 2003 between an unnamed plants from the inventor's breeding program as the female parent, reference no. H99-9C, and male parent, reference no. H02-09A. 'Stainless Steel' was selected as a single unique plant in May 2004 amongst the seedlings that resulted from the above cross.

Asexual reproduction of the new cultivar was first accomplished by division in Scottsdale, Pa. in September 2007. Asexual reproduction of the new cultivar by division, cuttings, and tissue culture has shown that the unique features are stable and reproduced true to type in successive generations.

SUMMARY OF THE INVENTION

The following traits have been repeatedly observed and represent the characteristics of the new cultivar. These attributes in combination distinguish 'Stainless Steel' as a new and unique cultivar of *Heuchera*.

1. 'Stainless Steel' exhibits foliage that emerges silver in color and heavily suffused with red-purple and matures to silver with green veins, lower leaf surface is dark red-purple.
2. 'Stainless Steel' exhibits flowers that are comparatively large, well shaped, and white in color.
3. 'Stainless Steel' exhibits a well-proportioned plant form.
4. 'Stainless Steel' exhibits evergreen foliage that is weather resistant with good tolerance to wind and rain.
5. 'Stainless Steel' exhibits good garden performance.

'Stainless Steel' can be readily distinguished from its parent plants. The female parent, H99-09C, differs from 'Stainless Steel' in having leaves that are more rounded in outline with smaller lobes and silver in color with purple-brown veins, and in having inflorescences that are taller in height. The male parent, H02-09A, differs from 'Stainless Steel' in having leaves with lower surfaces that are green in color and upper surfaces that are underlain with green, in having new foliage that is not suffused with red-purple, in having flowers that are less symmetrical, in having white sepals that are not shaded with red-purple, and in having inflorescences that are taller in height.

'Stainless Steel' can be compared most closely to the cultivar 'Jade Glass' (U.S. Plant Pat. No. 13,137). 'Jade Gloss' differs from 'Stainless Steel' in having smaller leaves that are silver in color with wide purple-brown veins, in having larger leaves, in having longer petioles, in having flower stalks held more erect, and in having smaller flowers. 'Stainless Steel' can be compared to 'Dark Chocolate' (U.S. Plant patent application Ser. No. 13/136,148). 'Dark Chocolate' is similar in having flowers that are comparatively large and well shaped, in having evergreen foliage that is weather resistant with good tolerance to wind and rain, and in having good garden performance. 'Dark Chocolate' differs from 'Stainless Steel' in having foliage that is dark purple-bronze with silver mottling and in having flowers that are pink in color.

BRIEF DESCRIPTION OF THE DRAWING

The accompanying colored photographs illustrate the overall appearance and distinct characteristics of the new *Heuchera*.

The photograph in FIG. 1 was taken of a one-year old plant as grown in a greenhouse in Scottsdale, Pa. and provides a side view of 'Stainless Steel' in bloom.

Figure 1:
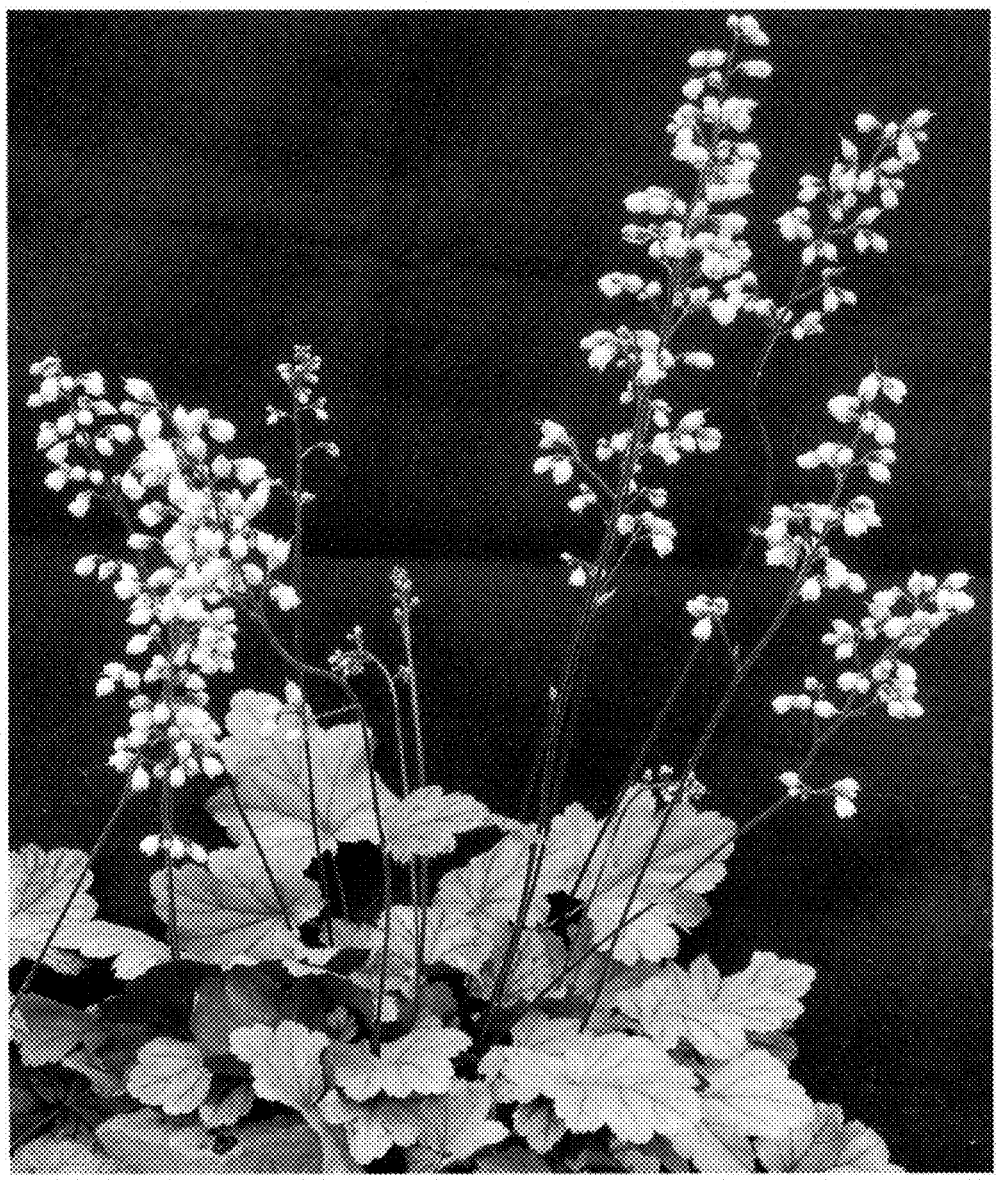
Figure 2:
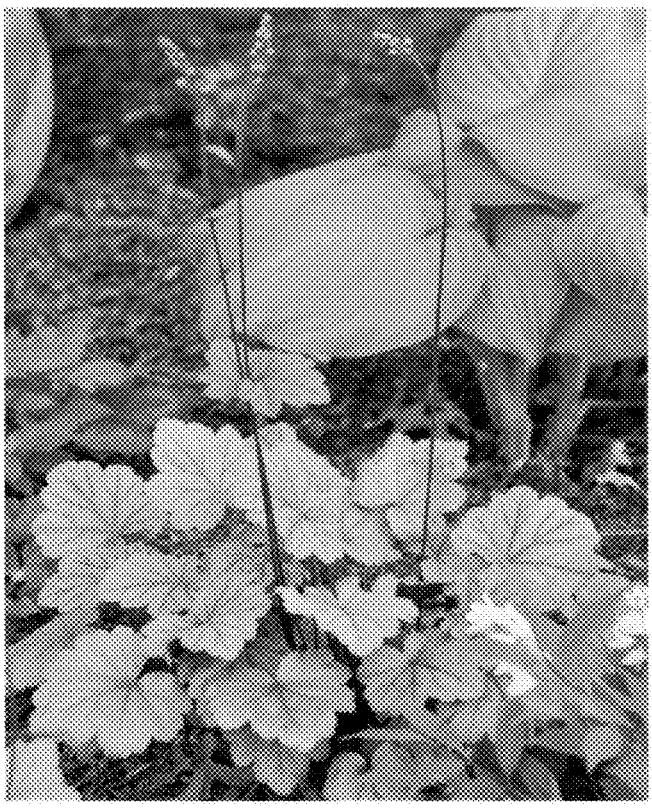
Figure 3:
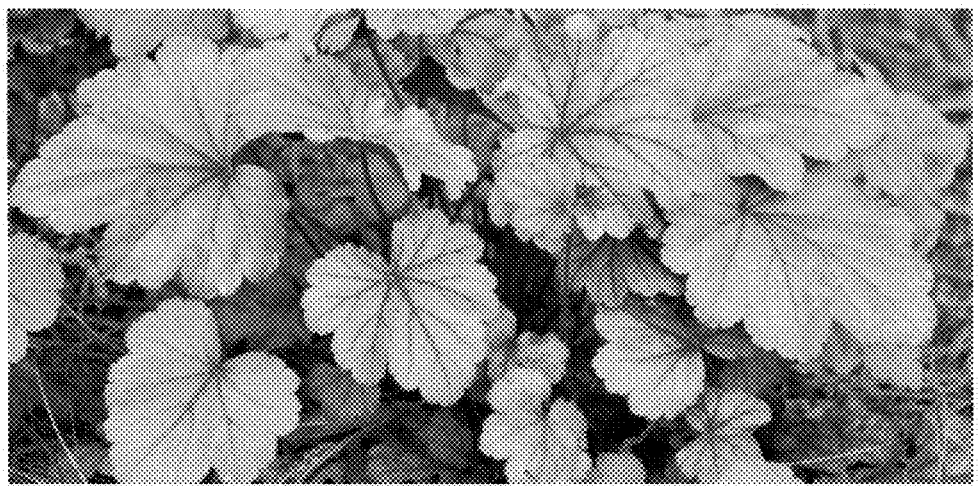

The photographs in FIG. 2 and FIG. 3 were taken of a two year-old plant as grown in a garden in Baltimore, Md.

FIG. 2 provides a side view of 'Stainless Steel' just beginning to bloom.

FIG. 3 provides a close-up view of the foliage of 'Stainless Steel'.

The colors in the photograph may differ slightly from the color values cited in the detailed botanical description, which accurately describe the colors of the new *Heuchera*.

DETAILED BOTANICAL DESCRIPTION OF THE PLANT

The following is a detailed description of one year-old plants of the new cultivar as grown in one-gallon containers in a glass greenhouse in Scottsdale, Pa. The plants were grown under average day temperatures of 26° C. (summer) to 15° C. (winter) and average night temperatures of 15° C. (summer) to 5° C. (winter). The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Plant type.*—Herbaceous perennial.

*Plant habit.*—Clump-forming, mounded, evergreen foliage.

*Height and spread.*—Average of 35 to 45 cm in height (in bloom) and 30 to 40 cm in diameter.

*Blooming period.*—May to June in Scottsdale, Pa.

*Hardiness.*—At least tolerant between −30° C. and 45° C.

*Environmental stresses.*—Excellent tolerance to rain and wind.

*Diseases and pests.*—Disease free in the conditions tested, no susceptibility or resistance to pests has been observed.

*Root description.*—Finely fibrous roots on woody rootstalks.

*Branching habit.*—Basal rosettes.

*Propagation.*—Cuttings and tissue culture preferred.

*Root initiation.*—Roots appear in rooting media in 15 days at 23° C. in summer and in 21 days at 17° C. in winter.

*Root development.*—Rooted cuttings or liners develop in 45 days at 23° C. and in 60 days at 17° C.

*Growth rate.*—Vigorous.

Foliage description:

*Leaf shape.*—Rounded and cordate.

*Leaf division.*—Simple.

*Leaf base.*—Auriculate.

*Leaf apex.*—Broadly obtuse, lobed.

*Leaf venation.*—Reticulate, color; upper surface 189A, lower surface 187B.

*Leaf margins.*—7-lobed with lobe margins ciliate and crenate.

*Leaf attachment.*—Petiolate.

*Leaf arrangement.*—Rosettes.

*Leaf orientation.*—Held almost horizontal to petiole.

*Leaf surface.*—Upper surface slightly rough to touch, upper and lower surface is slightly pubescent.

*Leaf color.*—Young upper surface; 189C suffused with 187D, young lower surface; 187D, mature upper surface; 189C underlain with 187B, mature lower surface; 187B.

*Leaf size.*—Average of 8.5 cm in length and width.

*Petioles.*—Round in shape, average of 13.5 cm in length and 2 mm in width, 189C underlain with 187D in color, surface is slightly pubescent.

Flower description:

*Inflorescence type.*—Numerous small bell-shaped flowers arranged on open narrow panicles.

*Inflorescence size.*—Average of 50 cm in height and 4.5 to 5 cm in width.

*Flower fragrance.*—None.

*Flower quantity.*—Average of 75 to 100 per panicle, 12 to 15 panicles per plant, 1200 to 1500 flowers per plant.

*Flower lastingness.*—Average of 7 days per flower, individual panicles bloom for about 2 weeks, flowers persistent.

*Flower buds.*—Obovate in shape, average of 6 mm in length and 4 mm in diameter, color is 199D overlain with 62C with glandular hairs 62A.

*Flower aspect.*—Held outward to slightly downward.

*Flower shape.*—Campanulate.

*Flower size.*—Average of 8 mm in diameter and 10 mm in depth.

*Petals.*—5, spatulate in shape, symmetrically arranged, margin is finely dentate, apex is acute, about 4 mm in length and 2.5 mm in width, upper surface is glabrous, lower surface is pubescent with glandular hairs, color; upper surface when opening and fully mature; NN155B, lower surface when opening and fully open; NN155B scattered with glandular hairs with 62A.

*Calyx.*—Tubular in shape, 10 mm in length and 8 mm in diameter.

*Sepals.*—5, fused into tube, average of 10 mm in length and 8 mm in width, margin is entire, apex is obtuse, base is fused, color upper surface; NN155B, color lower surface; NN155B, suffused with 62A with glandular hairs 62A.

*Rachis* (*flower scape*).—Strong, average of 48 cm in length and 2 mm in diameter, pilose surface, 187B in color, held a 60° to 90° angle.

*Peduncles.*—Strong, average of 1 cm in length and 0.5 mm in diameter, surface pubescent with glandular hairs, 187B in color, held at about a 45° angle.

*Pedicels.*—Strong, average of 2.5 mm in length and 0.2 mm in width, surface pubescent with glandular hairs, 194B in color with glandular hairs 187B, held at about a 60° angle.

*Bracts.*—Average of 2 mm in length and 1 mm in width, lanceolate in shape, margin is serrate, apex is acute, upper and lower surface is pubescent with glandular hairs, upper and lower surface 57A in color.

Reproductive organs:

*Gynoecium.*—2 Pistils, about 9 mm in length, stigmas are round in shape, 157A in color, styles are about 5 mm in length and 157D in color, ovary is 157D in color.

*Androcoecium.*—Average of 5 stamens, anthers are oval in shape, average of 0.6 mm to 1 mm in length and 23C in color, filaments are about 0.6 mm in length and N155B to N155C in color, moderate amount of pollen, 23C in color.

*Seed.*—High in quantity, 0.6 mm in length, 0.3 mm in diameter, 203D in color.

It is claimed:

1. A new and distinct cultivar of *Heuchera* plant named 'Stainless Steel' as herein illustrated and described.

* * * * *